United States Patent
Schankel et al.

(10) Patent No.: US 11,583,485 B2
(45) Date of Patent: Feb. 21, 2023

(54) ANTIPERSPIRANT / DEODORANT COMPOSITIONS INCLUDING BIODEGRADABLE AMINO CARBOXYLATES AND METHODS FOR THE SAME

(71) Applicant: Colgate-Palmolive Company, New York, NY (US)

(72) Inventors: Daniel Schankel, North Brunswick, NJ (US); Viktor Dubovoy, Cresskill, NJ (US); Richard Adams, South Orange, NJ (US); Sandra Wadeer, Flanders, NJ (US); Christine Boyke, Somerset, NJ (US); Long Pan, Somerset, NJ (US); Ravi Subramanyam, Belle Mead, NJ (US)

(73) Assignee: Colgate-Palmolive Company, New York, NY (US)

(*) Notice: Subject to any disclaimer, the term of this patent is extended or adjusted under 35 U.S.C. 154(b) by 0 days.

(21) Appl. No.: 16/771,519

(22) PCT Filed: Dec. 14, 2017

(86) PCT No.: PCT/US2017/066259
§ 371 (c)(1),
(2) Date: Jun. 10, 2020

(87) PCT Pub. No.: WO2019/117903
PCT Pub. Date: Jun. 20, 2019

(65) Prior Publication Data
US 2021/0177715 A1    Jun. 17, 2021

(51) Int. Cl.
| | |
|---|---|
| *A61K 8/26* | (2006.01) |
| *A61K 8/02* | (2006.01) |
| *A61K 8/04* | (2006.01) |
| *A61K 8/06* | (2006.01) |
| *A61K 8/44* | (2006.01) |
| *A61Q 15/00* | (2006.01) |
| *A61K 8/41* | (2006.01) |

(52) U.S. Cl.
CPC .............. *A61K 8/26* (2013.01); *A61K 8/0229* (2013.01); *A61K 8/042* (2013.01); *A61K 8/062* (2013.01); *A61K 8/064* (2013.01); *A61K 8/44* (2013.01); *A61Q 15/00* (2013.01); *A61K 8/41* (2013.01); *A61K 2800/874* (2013.01)

(58) Field of Classification Search
None
See application file for complete search history.

(56) References Cited

U.S. PATENT DOCUMENTS

| | | |
|---|---|---|
| 6,107,518 A | 8/2000 | Groth et al. |
| 8,318,806 B2 | 11/2012 | Mabrouk |
| 9,724,286 B2 | 8/2017 | Banowski et al. |
| 10,111,817 B2 | 10/2018 | Dubovoy et al. |
| 2008/0234173 A1 | 9/2008 | Warr et al. |
| 2016/0206534 A1 | 7/2016 | Banowski |

FOREIGN PATENT DOCUMENTS

| | | | |
|---|---|---|---|
| CN | 1494409 | 5/2004 | |
| CN | 1494410 | 5/2004 | |
| RU | 2260419 | 9/2005 | |
| WO | WO-2016014011 A | * 1/2016 | ............ A61K 8/41 |

OTHER PUBLICATIONS

Benta Berry, 2013, "Deo Spray Superior Quality," Mintel Database GNPD AN: 2094967.
International Search Report and Written Opinion of the International Searching Authority in International Application No. PCT/US2017/066259, dated Jul. 12, 2018.
Pinto et al., 2014, "Biodegradable chelating agents for industrial, domestic, and agricultural applications—a review," Environmental Science and Pollution Research International 21(20):11893-11906.
Chen, "Environment-friendly organic chelating agent (I)," China Dyeing and Finishing No. 18, pp. 43-46, Sep. 15, 2010.

* cited by examiner

*Primary Examiner* — Sin J Lee

(57) ABSTRACT

Antiperspirant and/or deodorant compositions and methods for the same are provided. The compositions may include an antiperspirant active or a deodorant active, water, and a preservative system. The antiperspirant active may include aluminum, and the preservative system may include a biodegradable amino carboxylate. The methods may include substituting or replacing a conventional chelant, such as EDTA, with a biodegradable chelant, such as HIDS. The methods may also include applying one of the compositions to an axillary area of a person.

12 Claims, No Drawings

ANTIPERSPIRANT / DEODORANT COMPOSITIONS INCLUDING BIODEGRADABLE AMINO CARBOXYLATES AND METHODS FOR THE SAME

BACKGROUND

Synthetic aminopolycarboxylic acids, such as ethylenediaminetetraacetic acid (EDTA), may often be utilized in a variety of products and industrial applications. For example, EDTA is conventionally used to control solubility and precipitation of metal ions, and to boost the function of preservatives. EDTA may function by forming highly stable metal complexes with the metal ions, thereby discouraging side or unwanted chemical interactions/reactions with these metals ions. In consumer products, tetrasodium EDTA may often be incorporated into aqueous or water-based antiperspirant compositions to enhance a preservative system thereof, and reduce yellowing caused by free metal ions (e.g., iron ions).

While EDTA is generally considered nontoxic to mammals and aquatic organisms, the environmental impact of EDTA has raised concerns due in part to its overuse and its increased concentration in varying sources of water (e.g., streams, oceans, aquifers, etc.). For example, the high concentrations of EDTA in the sources of water may solubilize heavy metals from sediment and soil, thereby increasing the mobility of the heavy metals and upsetting the natural metal distribution in the environment. The increased mobility of the heavy metals in the sources of water may also pose an increased health risk (e.g., toxicity) to humans, plants, animals, and other organisms. Further, EDTA degrades relatively slowly; and thus, is not generally considered a chelants that is readily biodegradable.

What is needed, then, are improved antiperspirant/deodorant compositions including improved preservative systems that are free or substantially free of EDTA, and methods for replacing EDTA.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

Embodiments of the disclosure may provide a composition including an antiperspirant active, water, and a preservative system. The antiperspirant active may include aluminum. The preservative system may include a biodegradable amino carboxylate.

In at least one embodiment, the preservative system may be free or substantially free of ethylenediaminetetraacetic acid (EDTA) and salts thereof.

In at least one embodiment, the biodegradable amino carboxylate may be selected from a [S—S]-ethylenediaminedisuccinic acid (EDDS) or an alkali metal salt thereof, a 3-hydroxy-2,2'-iminodisuccinic acid (HIDS) or an alkali metal salt thereof, an iminodisuccinate (IDS) or an alkali metal salt thereof, or mixtures thereof.

In at least one embodiment, the preservative system may include HIDS.

In at least one embodiment, the preservative system may consist essentially of HIDS.

In at least one embodiment, the preservative system may consist of HIDS.

In at least one embodiment, the composition may exhibit an SEC chromatogram having as SEC Peak 4 area relatively greater than an SEC Peak 4 area of a composition including EDTA.

In at least one embodiment, the Peak 4/3 ratio is relatively greater than the Peak 4/3 ratio of a composition not including HIDS, such as IDS or EDTA.

In at least one embodiment, the composition may be an aqueous liquid in the form of a roll-on.

In at least one embodiment, the composition may include a deodorant active.

In at least one embodiment, the composition may be an oil in water liquid roll-on.

In at least one embodiment, the composition may be a water in oil gel.

In at least one embodiment, the composition may be a water in oil cream.

In at least one embodiment, the composition may have a total solids content of about 25 weight % or less.

In at least one embodiment, the water may be present in an amount that is at least about 20 weight % by weight of the composition.

Embodiments of the disclosure may also provide a method for any one of the compositions disclosed herein. The method may include applying any one of the compositions disclosed herein with an axillary area of a person.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

The present inventors have surprisingly and unexpectedly discovered that antiperspirant/deodorant compositions that replace or substitute tetrasodium EDTA with an iminodisuccinate, namely, 3-hydroxy-2,2'-iminodisuccinic acid (HIDS), in the preservative system exhibited enhanced Peak 4 as measured in size exclusion chromatography (SEC). The present inventors have also surprisingly and unexpectedly discovered that antiperspirant/deodorant compositions including biodegradable chelant, HIDS, exhibits improved efficacy as compared to other iminodisuccinates, namely, IDS. Particularly, the present inventors have surprisingly and unexpectedly discovered that antiperspirant/deodorant compositions including HIDS exhibited relatively greater Peak 4/3 ratios as compared to antiperspirant/deodorant compositions including IDS.

Compositions

Compositions disclosed herein may be or include antiperspirants and/or deodorant compositions. The antiperspirant and/or deodorant compositions may include an antiperspirant active (e.g., aluminum active), a preservative system, and water. The preservative system may be or include one or more amino carboxylates or iminodisuccinates, and may be free or substantially free of ethylenediaminetetraacetic acids (EDTA) and salts thereof (e.g., tetrasodium EDTA).

The composition may be an aqueous liquid (e.g., roll-on), a gel, an aerosol, or a cream, which may often be included in the definition of a "soft solid". In the liquid form, the composition may be formulated as a roll-on product. In the liquid form, the composition may be an oil-in-water emulsion or a water-in-oil emulsion. The forms of these compositions may be suspensions or emulsions. In one implementation, the composition may be an oil-in-water liquid emulsion. The liquid may be contained in any roll-on dispenser having a ball for applying the composition to surfaces of skin. For example, the composition of the invention may be an oil-in-water liquid roll-on or a water-in-oil gel or a water-in-oil cream.

The antiperspirant active may be or include, but is not limited to, aluminum chlorohydrate, aluminum chloride, aluminum sesquichlorohydrate, aluminum-zirconium hydroxychlorides, complexes or adducts of the above-mentioned active ingredients with glycol, such as propylene glycol (e.g., "Rehydrol" II, which is commercially available from Reheis Chemical Co. of Berkeley Heights, N.J.), or the like, or mixtures and combinations thereof. The aluminum-zirconium salts may be combined with neutral amino acids, such as glycine, to prepare an antiperspirant active (e.g., aluminum-zirconium tetrachlorohydrex Gly).

The antiperspirant active may also include, but is not limited to, an aluminum salt and/or an aluminum-zirconium salt stabilized by betaine and a calcium salt, as discussed in U.S. Pat. No. 7,704,531 to Tang et al., the contents of which are incorporated herein to the extent consistent with the present disclosure. The antiperspirant active may have a low metal to chloride ratio. Illustrative antiperspirant actives having a low metal to chloride ratio are discussed in U.S. Pat. No. 6,375,937 to Chopra et al. and U.S. Patent Application Publication No. 2004/0109833 to Tang et al., the contents of which are incorporated herein to the extent consistent with the present disclosure.

In at least one implementation, an aluminum zirconium tetrasalt or octasalt free of glycine may be used where the aluminum zirconium salt is stabilized by betaine and may have a metal to chloride ratio of about 0.9:1 to about 1.3:1, about 0.9:1 to about 1.2:1, or about 0.9:1 to about 1.1:1. For the tetrasalt, the Al/Zr atomic ratio may be about 3.2:1 to about 4.1:1.0 and the betaine:zirconium mole ratio may be about 0.2:1 to about 3.0:1, or about 0.4:1 to about 1.5:1. Another salt that may be used may be an aluminum chloride salt buffered by betaine, wherein the salt has a metal to chloride ratio of 0.9:1 to 1.3:1, about 0.9:1 to about 1.2:1, or about 0.9:1 to about 1.1:1. For the octasalt the Al/Zr atomic ratio may be about 6.2:1 to about 10.0:1 and the betaine:zirconium mole ratio may be about 0.2:1 to about 3.0:1, or about 0.4:1 to about 1.5:1. In the case of a salt that contains zirconium, the betaine may be incorporated during the synthesis of the salt so as to maximize the stabilizing effect of the betaine. In at least one example, betaine may be post added to a glycine-free salt along with additional active phase ingredients to form a betaine stabilized active. Illustrative glycine-free low metal to chloride ratio tetra- and octa-salts may include, but are not limited to, Rezal™ AZP 955 CPG and Rezal™ AZP 885, both of which are commercially available from Reheis Chemical Co. of Berkeley Heights, N.J.

In at least one implementation, the antiperspirant active may be a calcium salt stabilized antiperspirant active. Examples of calcium salt stabilized antiperspirant actives may be found in U.S. Patent Application Publication No. 2006/0204463 to Tang et al., the contents of which is incorporated herein to the extent consistent with the present disclosure.

It should be appreciated that the antiperspirant active may include any one or more of the Category I active antiperspirant ingredients listed in the Food and Drug Administration's Monograph on Antiperspirant Drug Products for Over-The-Counter Human Use (Monograph). It should further be appreciated that any new ingredient, not listed in the Monograph may be utilized as an antiperspirant active. For example, the antiperspirant active may be or include, but is not limited to, aluminum nitratohydrate and its combination with zirconyl hydroxychlorides and nitrates, or aluminum-stannous chlorohydrates. Further illustrative examples of antiperspirant actives may be or include, but are not limited to, astringent salts of aluminum, astringent salts of zirconium, aluminum bromohydrate, aluminum chlorohydrate, aluminum dichlorohydrate, aluminum sesquichlorohydrate, aluminum chlorohydrex PG, aluminum dichlorohydrex PG, aluminum sesquichlorohydrex PG, aluminum chlorohydrex PEG, aluminum dichlorohydrex PEG, aluminum sesquichlorohydrex PEG, aluminum chloride, aluminum sulfate, aluminum zirconium chlorohydrate, aluminum zirconium trichlorohydrate, aluminum zirconium tetrachlorohydrate, aluminum zirconium pentachlorohydrate, aluminum zirconium octachlorohydrate, aluminum zirconium tetrachlorhydrex propylene glycol, aluminum zirconium trichlorohydrex Gly, aluminum zirconium tetrachlorohydrex Gly, aluminum zirconium pentachlorohydrex Gly, aluminum zirconium octachlorohydrex Gly, buffered aluminum sulfate, potassium alum, sodium aluminum chlorohydroxy lactate, or the like, or mixtures and combinations thereof. In a preferred implementation, the antiperspirant active includes at least aluminum chlorohydrate.

The antiperspirant and/or deodorant composition may include any one or more suitable deodorant actives. Illustrative deodorant actives, may include, but are not limited to, antimicrobial actives, alcohols, 2,4,4'-trichloro-2'-hydroxy diphenyl ether (e.g., Triclosan), octoxyglycerin (SENSIVA™ SC 50), benzethonium chloride, polyhexamethylene biguanides, triethylcitrate, 2-amino-2-methyl-1-propanol (AMP), cetyl-triethylammomium bromide, cetyl pyridinium chloride, bactericides, bacteriostats, or the like, or mixtures and combinations thereof.

The amount of aluminum present in the antiperspirant/deodorant composition, as provided by the antiperspirant active, may vary widely. In at least one implementation, the amount of the aluminum present in the antiperspirant/deodorant composition, as provided by the antiperspirant active, may be from about 1 weight % to about 6 weight %, based on a total weight to the composition. For example, the amount of the aluminum present in the antiperspirant/deodorant composition, as provided by the antiperspirant active, may be from about 1 weight %, about 1.2 weight %, about 1.4 weight %, about 1.6 weight %, about 1.8 weight %, about 2 weight %, about 2.2 weight %, about 2.4 weight %, about 2.6 weight %, about 2.8 weight %, about 3 weight %, about 3.2 weight %, or about 3.4 weight % to about 3.6 weight %, about 3.8 weight %, about 4 weight %, about 4.2 weight %, about 4.4 weight %, about 4.6 weight %, about 4.8 weight %, about 5 weight %, about 5.2 weight %, about 5.4 weight %, about 5.6 weight %, about 5.8 weight %, about 6 weight %. In another example, the amount of the aluminum present in the antiperspirant/deodorant composition, as provided by the antiperspirant active, may be from about 1 weight % to about 6 weight %, about 1.2 weight % to about 5.8 weight %, about 1.4 weight % to about 5.6 weight %, about 1.6 weight % to about 5.4 weight %, about 1.8 weight % to about 5.2 weight %, about 2 weight % to about 5 weight %, about 2.2 weight % to about 4.8 weight %, about 2.4 weight % to about 4.6 weight %, about 2.6 weight % to about 4.4 weight %, about 2.8 weight % to about 4.2 weight %, about 3 weight % to about 4 weight %, about 3.2 weight % to about 3.8 weight %, or about 3.4 weight % to about 3.6 weight %.

The preservative system may be or include one or more preservatives or chelants. The one or more chelants may be or include, but are not limited to, amino carboxylates. Illustrative amino carboxylates may be or include biodegradable amino carboxylates. As used herein, "biodegradable chelants" or "biodegradable amino carboxylates" may refer to materials that may be used to control unwanted reactions (e.g., side reactions) of metal ions that may possess the ability of being decomposed by living organisms (e.g., bacteria). As used herein, "biodegradable chelants" may also refer to a chelants that exhibits a biodegradation percentage of at least 50%, at least 55%, at least 60%, at least 65%, at least 70%, or more according to the experimental method of either ISO14851, ISO14852, ISO14855 or OECD Guidelines for Testing of Chemicals (301C, Modified MITI Test).

Illustrative biodegradable amino carboxylates may be or include, but are not limited to, a [S—S]-ethylenediaminedisuccinic acid (EDDS) or an alkali metal salt thereof, (e.g., a sodium salt of [S—S]-ethylenediaminedisuccinic acid), a 3-hydroxy-2,2'-iminodisuccinic acid (HIDS) or an alkali metal salt thereof (e.g., tetrasodium 3-hydroxy-2,2'-iminodisuccinate), an iminodisuccinate (IDS) or an alkali metal salt thereof, or the like, or any mixture or combination thereof. In a preferred implementation, the preservative system includes tetrasodium 3-hydroxy-2,2'-iminodisuccinate, which may be represented by formula (1).

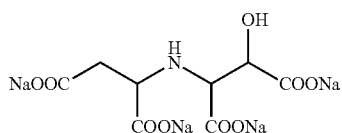

(I)

The concentration or amount of the chelants (e.g., HIDS) present in the antiperspirant/deodorant compositions may vary widely. In at least one implementation, a molar ratio of aluminum (as provided by the antiperspirant active) to the chelants (e.g., HIDS) or the chelants to the aluminum may be from about 10:1 to about 250:1. For example, the molar ratio of aluminum to the chelants or the chelants to aluminum may be from about 10:1, about 20:1, about 30:1, about 40:1, about 50:1, about 60:1, about 70:1, about 80:1, about 90:1, about 100:1, about 110:1, or about 120:1 to about 130:1, about 140:1, about 150:1, about 160:1, about 170:1, about 180:1, about 190:1, about 200:1, about 210:1, about 220:1, about 230:1, about 240:1, about 250:1, or greater. In another example, the molar ratio of aluminum to the chelants or the chelants to aluminum may be from about 10:1 to about 250:1, about 20:1 to about 240:1, about 30:1 to about 230:1, about 40:1 to about 220:1, about 50:1 to about 210:1, about 60:1 to about 200:1, about 70:1 to about 190:1, about 80:1 to about 180:1, about 90:1 to about 170:1, about 100:1 to about 160:1, about 110:1 to about 150:1, or about 120:1 to about 140:1. In yet another example, the molar ratio of aluminum to the chelants or the chelants to aluminum may be about 10:1, about 10.5:1, about 11:1, about 11.5:1, about 12:1, about 12.5:1, about 13:1, about 13.5:1, about 14:1, about 14.5:1, about 15:1, about 15.5:1, about 16:1, about 16.5:1, about 17:1, about 17.5:1, about 18:1, about 18.5:1, about 19:1, about 19.5:1, about 20:1, about 20.5:1, about 21:1, about 21.5:1, about 22:1, about 22.5:1, about 23:1, about 23.5:1, about 24:1, about 24.5:1, about 25:1, about 26:1, about 27:1, about 28:1, about 29:1, about 30:1, about 35:1, about 40:1, about 45:1, about 50:1, about 55:1, about 60:1, about 65:1, about 70:1, about 75:1, about 80:1, about 85:1, about 90:1, about 95:1, about 100:1, about 110:1, about 120:1, about 130:1, about 140:1, about 150:1, about 160:1, about 170:1, about 180:1, about 190:1, about 200:1, about 210:1, about 220:1, about 230:1, about 240:1, or about 250:1.

In at least one implementation, the amount of the chelants present in the antiperspirant/deodorant composition may be from greater than 0 weight % to about 1 weight %. For example, the amount of the chelants present in the antiperspirant/deodorant composition may be from greater than 0 weight %, about 0.01 weight %, about 0.02 weight %, about 0.03 weight %, about 0.04 weight %, about 0.05 weight %, about 0.06 weight %, about 0.07 weight %, about 0.08 weight %, about 0.09 weight %, or about 0.10 weight % to about 0.11 weight %, about 0.12 weight %, about 0.13 weight %, about 0.14 weight %, about 0.15 weight %, about 0.16 weight %, about 0.17 weight %, about 0.18 weight %, about 0.19 weight %, or about 0.20 weight %. In another example, the amount of the chelants present in the antiperspirant/deodorant composition may be from greater than 0 weight %, about 0.05 weight %, about 0.10 weight %, about 0.15 weight %, about 0.20 weight %, about 0.25 weight %, about 0.30 weight %, about 0.35 weight %, about 0.40 weight %, about 0.45 weight %, or about 0.50 weight % to about 0.55 weight %, about 0.60 weight %, about 0.65 weight %, about 0.70 weight %, about 0.75 weight %, about 0.80 weight %, about 0.85 weight %, about 0.90 weight %, about 0.95 weight %, or about 1 weight %.

In yet another example, the amount of the chelants present in the antiperspirant/deodorant composition may be from greater than 0 weight % to less than 0.05 weight %, less than 0.10 weight %, less than 0.15 weight %, less than 0.20 weight %, less than 0.25 weight %, less than 0.30 weight %, less than 0.35 weight %, less than 0.40 weight %, less than 0.45 weight %, less than 0.50 weight %, less than 0.55 weight %, less than 0.60 weight %, less than 0.65 weight %, less than 0.70 weight %, less than 0.75 weight %, less than 0.80 weight %, less than 0.85 weight %, less than 0.90 weight %, less than 0.95 weight %, or less than 1 weight %. In another example, the amount of the chelants present in the antiperspirant/deodorant composition may be from greater than 0 weight % to about 0.20 weight %, about 0.01 weight % to about 0.19 weight, about 0.02 weight % to about 0.18 weight %, about 0.03 weight % to about 0.17 weight %, about 0.04 weight % to about 0.16 weight %, about 0.05 weight % to about 0.15 weight %, about 0.06 weight % to about 0.14 weight %, about 0.07 weight % to about 0.13 weight %, about 0.08 weight % to about 0.12 weight %, about 0.09 weight % to about 0.11 weight %, or about 0.10 weight %. In yet another example, the amount of the chelants present in the antiperspirant/deodorant composition may be less than or equal to 0.01 weight %, less than or equal to 0.02 weight %, less than or equal to 0.03 weight %, less than or equal to 0.04 weight %, less than or equal to 0.05 weight %, less than or equal to 0.06 weight %, less than or equal to 0.07 weight %, less than or equal to 0.08 weight %, less than or equal to 0.09 weight %, less than or equal to 0.10 weight %, less than or equal to 0.11 weight %, less than or equal to 0.12 weight %, less than or equal to 0.13 weight %, less than or equal to 0.14 weight %, less than or equal to 0.15 weight %, less than or equal to 0.16 weight %, less than or equal to 0.17 weight %, less than or equal to 0.18 weight %, less than or equal to 0.19 weight %, or less than or equal to 0.20 weight %.

In at least one example, the amount of the chelants present in the antiperspirant/deodorant composition may be from about 0.0001 weight %, about 0.05 weight %, about 0.1 weight %, about 0.15 weight %, about 0.2 weight %, about 0.25 weight %, about 0.3 weight %, about 0.35 weight %, about 0.4 weight %, about 0.45 weight %, or about 0.5 weight % to about 0.55 weight %, about 0.6 weight %, about 0.65 weight %, about 0.7 weight %, about 0.75 weight %, about 0.8 weight %, about 0.85 weight %, about 0.9 weight %, about 0.95 weight %, or about 1 weight %. In another example, the amount of the chelants present in the antiperspirant/deodorant composition may be from about 0.0001 weight % to about 1 weight %, about 0.05 weight % to about 0.95 weight %, about 0.1 weight % to about 0.9 weight %, about 0.15 weight % to about 0.85 weight %, about 0.2 weight % to about 0.8 weight %, about 0.25 weight % to about 0.75 weight %, about 0.3 weight % to about 0.7 weight %, about 0.35 weight % to about 0.65 weight %, about 0.4 weight % to about 0.6 weight %, about 0.45 weight % to about 0.55 weight %, or about 0.5 weight %. In yet another example, the amount of the chelants present in the antiperspirant/deodorant composition may be greater than 0 weight % and less than or equal to 0.0001 weight %, less than or equal to 0.05 weight %, less than or equal to 0.1 weight %, less than or equal to 0.15 weight %, less than or equal to 0.2 weight %, less than or equal to 0.25 weight %, less than or equal to 0.3 weight 0, less than or equal to 0.35 weight %, less than or equal to 0.4 weight %, less than or equal to 0.45 weight %, less than or equal to 0.5 weight %, less than or equal to 0.55 weight %, less than or equal to 0.6 weight 0, less than or equal to 0.65 weight %, less than or equal to 0.7 weight %, less than or equal to 0.75 weight %, less than or equal to 0.8 weight %, less than or equal to 0.85 weight N, less than or equal to 0.9 weight %, less than or equal to 0.95 weight %, or less than or equal to 1 weight %.

In at least one implementation, the antiperspirant and/or deodorant compositions and the preservative systems thereof may be free or substantially free of ethylenediaminetetraacetic acids (EDTA) and salts thereof (e.g., tetrasodium EDTA). As used herein, "free" or "substantially free" may refer to a composition, component, or phase that contains less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight %, based on a total weight of the composition.

Any one or more suitable and/or compatible surfactants may be used in the antiperspirant and/or deodorant compositions, and may be included in any desired amount. In at least one implementation, the amount of surfactant may be from about 2 weight % to about 12 weight %, about 3 weight % to about 10 weight %, or about 2 weight % to about 5 weight %, based on a total weight of the composition. In an exemplary embodiment, the antiperspirant and/or deodorant composition is provided as an oil-in-water roll-on composition, and the one or more surfactants are present in an amount of from about 2 weight % to about 5 weight %, based on a total weight of the composition.

The one or more surfactants may be or include, but are not limited to, nonionic surfactants, silicone surfactants, or the like, or mixtures and combinations thereof. Illustrative nonionic surfactants may be or include, but are not limited to, sorbitan esters and ethoxylated sorbitan esters (e.g., PEG-20 sorbitan isostearate, sorbitan monolaurate, polysorbate-20, polysorbate-40, polysorbate-60, polysorbate-80, etc.), ethoxylates (e.g., Ceteth-20, PEG-30 castor oil, PEG-40 hydrogenated castor oil, PEG-60 hydrogenated castor oil, Laureth-7, Isolaureth-6, Steareth-10, Steareth-20, Steareth-21, Steareth-100, Ceteareth-12, Oleth-5, Oleth-10, etc.), ethoxylated adducts (e.g., PEG-25 stearate, glyceryl stearate, PEG-100 stearate, etc.), PEG esters (e.g., PEG-8 oleate, PEG-8 laurate, PEG-8 dilaurate, PEG-12 dilaurate, PEG-80 diisostearate, PEG-40 stearate, etc.), propoxylates (e.g., PPG-10 butanediol, PPG-50 oleyl ether, PPG-2-ceteareth-9, PPG-3-deceth-3, PPG-5-ceteth-20, etc.), ethoxylated modified triglycerides (e.g., PEG-20 corn glycerides, PEG-12 palm kernel glycerides, etc.), alkylphenol aromatic ethoxylates (e.g., dinonylphenol ethoxylate with 9 moles of EO, octylphenol ethoxylate with 20 moles of EO, octylphenol ethoxylate with 40 moles of EO, etc.), block copolymers that are alkoxylated glycols having ethoxylated and propoxylated segments (e.g., POLOXAMER™ 182 and 234, POLOXAMER™ 105 Benzoate, MEROXAPOL™ 174, etc.), and the like, and mixtures or combinations thereof. In a preferred implementation, the nonionic surfactant may be selected such that the antiperspirant and/or deodorant composition has an hydrophilic-lipophilic balance (HLB) value of from 8 to 16, or preferably an HLB of from 8 to 12.

In one implementation, the nonionic surfactant may be selected from ethoxylated nonionic surfactants and propoxylated nonionic surfactants. Illustrative ethoxylated nonionic surfactants and propoxylated nonionic surfactants may include, but are not limited to, Steareth 2, Steareth 20, Steareth 21, or the like, and mixtures or combinations thereof. In an exemplary implementation, a combination of a surfactant having an HLB value of about 2 to about 8 (e.g., Steareth 2) and a surfactant having an HLB of about 9 to about 18 (e.g., Steareth 20 and 21) may be utilized. For example, in an oil-in-water antiperspirant and/or deodorant composition, the surfactants may include a combination of Steareth 2 and Steareth 20 and/or 21.

Illustrative silicone surfactants may be found in U.S. Pat. No. 6,485,716 to Fei et al., the contents of which are incorporated herein by reference to the extent consistent with the present disclosure. Illustrative silicone surfactants may include, but are not limited to, silicone polyglucosides (e.g., octyl dimethicone ethoxy glucoside) and silicone copolyols having an HLB value less than or equal to 8. Illustrative silicon copolyols may be or include, but are not limited to, copolyols of formula (II) and (III).

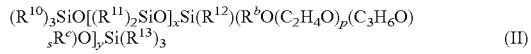

where each of $R^{10}$, $R^{11}$, $R^{12}$, and $R^{13}$ may be the same or different and each may be chosen from a C1-C6 alkyl; $R^b$ is the radical —$C_mH_{2m}$—; $R^c$ is a terminating radical which may be hydrogen, an alkyl group of one to six carbon atoms, an ester group such as acyl, or an aryl group such as phenyl; m has a value of two to eight; p and s have values such that the oxyalkylene segment —$(C_2H_4O)_p$—$(C_3H_6O)_s$— has a molecular weight in the range of about 200 to about 5,000; the segment preferably having fifty to one hundred mole percent of oxyethylene units —$(C_2H_4O)_p$— and one to fifty mole percent of oxypropylene units —$(C_3H_6O)_s$—; x has a value of about 8 to about 400; and y has a value of 2 to 40. Preferably each of $R^{10}$, $R^{11}$, $R^{12}$, and $R^{13}$ is a methyl group; $R^c$ is H; m is preferably three or four whereby the group $R^b$ is most preferably the radical —$(CH_2)_3$—; and the values of p and s are such as to provide a molecular weight of the oxyalkylene segment —$(C_2H_4O)_p$—$(C_3H_6O)_s$— of between about 1,000 to 3,000. In one embodiment, p and s may have a value of about 18 to about 28. In a preferred implementation, the silicone copolyol may be dimethicone copolyol.

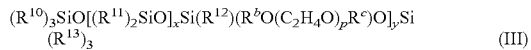

where p may have a value of about 6 to about 16; x may have a value of about 6 to about 100; and y may have a value of about 1 to about 20, and remaining moieties may be define as in formula (II).

It should be appreciated that in both Formulas II and III, the siloxane-oxyalkylene copolymers may, in alternate embodiments, take the form of endblocked polyethers in which the linking group $R^b$, the oxyalkylene segments, and the terminating radical $R^c$ occupy positions bonded to the ends of the siloxane chain, rather than being bonded to a silicon atom in the siloxane chain. Accordingly, one or more of the $R^{10}$, $R^{11}$, $R^{12}$, and $R^{13}$ substituents that are attached to the two terminal silicon atoms at the end of the siloxane chain may be substituted with the segment —$R^b$—O—$(C_2H_4O)_p$—$(C_3H_6O)_s$—$R^c$ or with the segment —$R^b$—O—$(C_2H_4P)_p$—$R^c$. In some instances, it may be desirable to provide the segment —$R^b$—O—$(C_2H_4O)_p$—$(C_3H_6O)_s$—$R^c$ or the segment —$R^b$—O—$(C_2H_4O)_p$—$R^c$ at locations which are in the siloxane chain as well as at locations at one or both of the siloxane chain ends.

Illustrative dimethicone copolyols may include, but are not limited to, DOW CORNING 5225C (a 10% dimethicone copolyol in cyclomethicone) or DOW CORNING 2-5185C (a 45-49% dimethicone copolyol in cyclomethicone), both of which are commercially available from Dow Corning Corporation of Midland, Mich., SILWET L-7622, which is commercially available from Witco Corporation of Greenwich, Conn., ABIL EM97 (an 85% dimethicone copolyol in D5 cyclomethicone), which is commercially available from Goldschmidt Chemical Corporation of Hopewell, Va., or the like, or mixtures and combinations thereof. It should also be noted that various concentrations of the dimethicone copolyols in cyclomethicone may be used. While a concentration of 10% in cyclomethicone is frequently seen commercially, other concentrations may be made by stripping off the cyclomethicone or adding additional cyclomethicone. The higher concentration materials such as DOW CORNING 2-5185 may be used in one embodiment.

In at least one implementation, about 0.5 weight % to about 5 weight %, or about 1 weight % to about 2 weight %, of a mixture of a 10% silicone copolyol, such as dimethicone copolyol, and cyclomethicone may be utilized. The mixture of the 10% silicone copolyol and the cyclomethicone may be provided in an amount such that the amount of the silicone copolyol in the antiperspirant and/or deodorant composition is from about 0.05 weight % to about 0.5 weight %, or about 0.1 weight %.

The composition may include one or more optional ingredients, such as a malodor counteracting alpha, beta-unsaturated ester, or mixtures thereof. The malodor counteracting materials may be provided in an amount of from about 0.05 weight % to about 0.45 weight %, based on a total weight of the composition. The alpha, beta-unsaturated ester malodor counteracting materials may be incorporated in the oil phase of the antiperspirant and/or deodorant composition. Illustrative malodor counteracting materials may be found in U.S. Pat. Nos. 6,610,648 and 6,495,097, both of which are incorporated herein to the extent consistent with the present disclosure.

The antiperspirant and/or deodorant composition may include additional materials, such as those that may commonly or conventionally be included in antiperspirant and/or deodorant compositions. For example, the antiperspirant and/or deodorant composition may also include, but are not limited, to monohydric alcohols, fragrances, water, other preservatives, humectants, natural and/or synthetic oils, other chelators, and the like, or mixtures and combinations thereof.

Water, such as deionized water, may be present in the composition (e.g., a liquid roll-on composition) in an amount to make a 100% by weight composition after all of the materials, including any optional materials, are added to the composition. In certain embodiments, the amount of water may be present in an amount of at least 20 weight %, at least 30 weight %, at least 40 weight %, at least 50 weight %, at least 60 weight %, at least 70 weight %, at least 80 weight %, at least 85 weight %, at least 90 weight %, or at least 95 weight %, based on a total weight of the composition.

A total solids in the antiperspirant/deodorant composition may be less than or equal to 30 weight %, less than or equal to 25 weight %, less than or equal to 20 weight %, less than or equal to 15 weight %, or less than or equal to 10 weight %. The total solids of the composition may the amount of non-volatile materials present in the composition. The percent solids may be measured by a CEM Smart System moisture/solids analyzer, which may utilize microwave energy to dry the compositions.

In at least one implementation, the antiperspirant and/or deodorant composition may include a single phase. In another implementation, the antiperspirant and/or deodorant composition may include two phases, such as a water phase and an oil phase. The water phase may include a solvent, such as water, actives, surfactants (e.g., hydrophilic surfactants), preservatives, and the like, and any combination thereof. The oil phase may include emollients and/or solvents, hydrophobic surfactants, antioxidants, fragrances, and the like, and any combination thereof.

It should be appreciated that the antiperspirant/deodorant compositions disclosed herein may be used by applying the composition to axillary areas of a person or subject.

Size exclusion chromatography ("SEC") or gel permeation chromatography ("GPC") are methods frequently used for obtaining information on polymer distribution in antiperspirant salt solutions. With appropriate chromatographic columns, generally five distinctive groups of polymer species may be detected in commercial aluminum chlorohydrex complexes ("ACH"), a complex of aluminum chlorohydrate and propylene glycol or polyethylene glycol, and aluminum zirconium glycine ("ZAG") complexes. These Peaks appear or identified in an SEC chromatogram as Peak 1, Peak 2, Peak 3, Peak 4, and a Peak known as Peak "5,6." Peak 1 is the larger Zr species (greater than 60 Angstroms). Peak 2 and Peak 3 are larger aluminum species. Peak 4 includes smaller aluminum species (e.g., aluminum oligomers or small aluminum cluster) and has been correlated with enhanced efficacy for both Al and Al/Zr salts. Peak 5, 6 is the smallest aluminum species. It should be appreciated that Peak 5, 6 and Peak 4 may each be indicators of enhanced efficacy for both Al and Al/Zr salts. As such, Peak 5, 6 and Peak 4 may often be combined with one another and referred to simply as "Peak 4". Various analytical approaches for characterizing the Peaks of ACH and various types of ZAG actives may be found in "Antiperspirant Actives-Enhanced Efficacy Aluminum-Zirconium-Glycine (AZG) Salts" by Dr. Allan H. Rosenberg (Cosmetics and Toiletries Worldwide, Fondots, D. C. ed., Hartfordshire, UK: Aston Publishing Group, 1993, pages 252, 254-256). The polymerization of the antiperspirant actives in aqueous solutions and the correspondent gelation process may be followed by monitoring the molecular weight profile of the polyoxohalides in time via SEC, as described in WO 2009/076591 and U.S. Publication No. 2010/0202993 to Pan, the contents of which are incorporated herein to the extent consistent with the present disclosure.

The relative retention time ("Kd") for each of these subject Peaks may vary depending on the experimental conditions, but the Peaks remain relative to each other. For example, an SEC chromatogram may be generated using the following parameters: WATERS® 600 analytical pump and controller, RHEODYNE® 77251 injector, PROTEIN-PAK® 125 (Waters) column, WATERS® 2414 Refractive Index Detector. 5.56 mM nitric acid mobile phase, 0.50 mL/min flow rate, 2.0 microliter injection volume. Date may be analyzed using WATER EMPOWER® software (Waters Corporation, Milford, Mass.). The concentration of the antiperspirant in solution does not affect the retention tie in the machine.

The design of modern antiperspirant salts aims at antiperspirant actives with high levels of low molecular weight Al and Zr species, which may be reflected in an SEC trace that has intense Peak 4, and low Peaks 1, 2, 3, and 5, 6 or low Peak 1, 2, 3 (e.g., when Peak 5, 6 is combined with Peak 4). Levels of the species corresponding to these Peaks are estimated based on the following ratios (or percentages):

$$fPi = \frac{Pi}{\sum Pj} \quad i = 1, 2, 3, 4, 5; j = 2, 3, 4, 5$$

where $f_{P_i}$ is the fraction of Peak i, and Pi and Pj are the intensity of Peaks Pi and Pj, respectively. The amount of low molecular weight Al species will be correlated with the fraction, $f_{P4}$, or percentage, FP4×100, of SEC-Peak 4. In brief, a preferred antiperspirant salt would have a very low $f_{P1}$, $f_{P2}$, $f_{P3}$, and/or $f_{P5}$, and a high $f_{P4}$ or a high $f_{P4}+f_{P5}$.

In at least one implementation, the intensity ratio of Peak 4 to Peak 3 may be at least 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, or greater.

In another implementation, the percentage of SEC Peak 4 of a total area of Peaks 1, 2, 3, 4, and 5, 6 in the SEC chromatogram may be at least 50%, at least 55%, at least 60%, at least 62%, at least 64%, at least 66%, at least 68%, at least 70%, at least 72%, at least 74%, at least 76%, at least 78%, at least 80%, at least 82%, at least 84%, at least 86%, at least 88%, at least 90%, at least 92%, at least 94%, at least 95%, at least 96%, at least 97%, at least 98%, at least 99%, at least 99.5%, or greater of a total area of Peaks 1, 2, 3, 4, and 5, 6.

In yet another implementation, the combined percentage of SEC Peak 4 and Peak 5 of a total area of Peaks 1, 2, 3, 4, and 5, 6 in the SEC chromatogram may be at least 50%, at least 55%, at least 60%, at least 62%, at least 64%, at least 66%, at least 68%, at least 70%, at least 72%, at least 74%, at least 76%, at least 78%, at least 80%, at least 82%, at least 84%, at least 86%, at least 88%, at least 90%, at least 92%, at least 94%, at least 95%, at least 96%, at least 97%, at least 98%, at least 99%, at least 99.5%, or greater, of a total area of Peaks 1, 2, 3, 4, and 5, 6.

In yet another implementation, the combined percentage of SEC Peak 4 and Peak 5 of a total area of Peaks 1, 2, 3, 4, and 5, 6 in the SEC chromatogram of the compositions disclosed herein may be relatively greater than the SEC Peak 4 and Peak 5 of a total area of Peaks 1, 2, 3, 4, and 5, 6 in the SEC chromatogram of conventional antiperspirant compositions including EDTA. For example, the SEC Peak 4 and Peak 5 may be at least 1% greater, at least 2% greater, at least 3% greater, at least 4% greater, at least 5% greater, at least 6% greater, at least 7% greater, at least 8% greater, at least 9% greater, at least 1°% greater, at least 15% greater, at least 20% greater, at least 25% greater, at least 30% greater, at least 35% greater, at least 40% greater, at least 45% greater, at least 50% greater, at least 55% greater, at least 60% greater, at least 65% greater, at least 70% greater, at least 75% greater, at least 80% greater, at least 85% greater, at least 90% greater, at least 95% greater, at least 100% greater, Methods The present disclosure may provide methods for reducing apparent perspiration including applying any one of the antiperspirant/deodorant compositions disclosed herein to an axillary area of a subject, user, or person, wherein the antiperspirant/deodorant composition reduces apparent perspiration.

The present disclosure may also provide methods for preparing an environmentally friendly personal care composition (e.g., antiperspirant/deodorant composition). The method may include substituting or replacing EDTA in conventional personal care compositions with a biodegradable chelants, such as an amino carboxylate or preferably HIDS. The method may also include combining, mixing, or otherwise contacting an antiperspirant active with a preservative system including an amino carboxylate, such as HIDS.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

To evaluate compositions utilizing HIDS as a chelants/preservative, aluminum chlorohydrate powder (ACH103; 25.4% Al) was combined with tetrasodium EDTA to prepare a control (1), and a 50.9 weight % solution of HIDS was used to prepare samples (2)-(5) with varying concentrations according to the amounts shown in Table 1. It should be appreciated that conventional roll-on antiperspirant compositions utilize tetrasodium EDTA in an amount of from about 0.20 weight % to about 0.25 weight %. As such, the control (1) was prepared with 0.20 weight % EDTA as a proper comparison.

TABLE 1

Sample Compositions for EDTA and HIDS

| Sample | Chelator (g)* | ACH (g) | Total (g) |
|---|---|---|---|
| 0.20% Na$_4$-EDTA; Control (1) | 0.0204 | 1.4633 | 10.0004 |
| 0.10% Na$_4$-HIDS (2) | 0.0190 | 1.4637 | 9.9999 |
| 0.20% Na$_4$-HIDS (3) | 0.0397 | 1.4640 | 9.9998 |
| 0.40% Na$_4$-HIDS (4) | 0.0791 | 1.4640 | 9.9997 |
| 0.80% Na$_4$-HIDS (5) | 0.1579 | 1.4631 | 9.9993 |

*Mass of chelants is mass of 50.9% solution needed for indicated concentration

Each of the samples (1)-(5) were evaluated via SEC, as described above. The results of the SEC analysis are summarized in Table 2.

TABLE 2

SEC Peak Area

| Sample | SEC Peak 4 Area (mV * min) | % Change |
|---|---|---|
| 0.20% Na$_4$-EDTA; Control (1) | 6.3506 | 0 |
| 0.10% Na$_4$-HIDS (2) | 6.5892 | 3.76 |
| 0.20% Na$_4$-HIDS (3) | 6.3796 | -0.46 |
| 0.40% Na$_4$-HIDS (4) | 5.6313 | -11.33 |
| 0.80% Na$_4$-HIDS (5) | 4.1107 | -35.27 |

As indicated in Table 2, HIDS surprisingly and unexpectedly demonstrated enhanced Peak 4 intensity at 0.10 weight %. As further indicated in Table 2, the enhanced Peak 4 was not prevalent at higher concentrations. For example, sample (3) with about 0.20 weight % HIDS exhibited an SEC Peak 4 at almost parity with the control (1), and the SEC Peak 4 area gradually decreased in the samples having increased HIDS (3)-(5). It was also observed that the SEC chromatogram of sample (3) exhibited degradation of Peak 3 into Peak 2. The results of this evaluation demonstrated the replacement of tetrasodium EDTA with tetrasodium HIDS in 12% anhydrous ACH formulations, and further demonstrated the surprisingly and unexpected enhancement of SEC Peak 4 when the HIDS is present in amounts less than 0.20 weight %.

Example 2

Compositions utilizing HIDS as a chelant/preservative were evaluated with compositions utilizing another iminodisuccinate-based chelants, namely, iminodisuccinate (IDS) as a chelant. Particularly, samples (6)-(11) having varying concentrations of IDS and HIDS were prepared according to the amounts shown in Table 3. To prepare the samples (6)-(11), a stock ACH solution was prepared by diluting 60.8 g of a 50% ACH solution with deionized (DI) water to 200.0 g. The 200 g ACH stock solution was then combined with the varying amounts of the HIDS or the IDS to prepare the samples (6)-(11).

TABLE 3

Sample Compositions for IDS and HIDS

| Sample | Chelator (g)* | ACH (g) | Total (g) |
|---|---|---|---|
| 0.10% Na$_4$-IDS (6) | 0.0805 | 28.937 | 29.0175 |
| 0.20% Na$_4$-IDS (7) | 0.1756 | 29.8648 | 30.0404 |
| 0.25% Na$_4$-IDS (8) | 0.2205 | 30.0125 | 30.233 |
| 0.10% Na$_4$-HIDS (9) | 0.0572 | 29.9776 | 30.0348 |
| 0.20% Na$_4$-HIDS (10) | 0.111 | 29.8718 | 29.9828 |
| 0.25% Na$_4$-HIDS (11) | 0.1411 | 29.8733 | 30.0144 |

Each of the samples (6)-(11) were exposed to accelerated aging conditions by placing the samples in an oven at 50° C. for four days. The samples (6)-(11) were then taken out of the oven and cooled to room temperature prior to SEC analysis. A 0.1 mL aliquot of each sample was diluted to 0.4 mL in a syringe and injected directly into the SEC instrument. The results of the SEC analysis are summarized in Table 4.

TABLE 4

SEC Peak Areas of ACH with 0.1-0.25% Chelator

| Samples | Peak 2 (%) | Peak 3 (%) | Peak 4 (%) | Peak 5 (%) | Peak 4/3 Ratio |
|---|---|---|---|---|---|
| 0.10% Na$_4$-IDS (6) | 15.99 | 56.32 | 26.80 | 0.89 | 0.48 |
| 0.20% Na$_4$-IDS (7) | 19.61 | 55.17 | 24.35 | 0.86 | 0.44 |
| 0.25% Na$_4$-IDS (8) | 21.44 | 54.85 | 22.87 | 0.85 | 0.42 |
| 0.10% Na$_4$-HIDS (9) | 17.49 | 53.79 | 27.72 | 1.00 | 0.52 |
| 0.20% Na$_4$-HIDS (10) | 21.22 | 51.12 | 26.75 | 0.92 | 0.52 |
| 0.25% Na$_4$-HIDS (11) | 19.35 | 53.03 | 26.56 | 1.06 | 0.50 |

It should be appreciated that the Peak 4/3 ratio is a key indicator of sweat reduction efficacy of commercial aluminum antiperspirant salts. As indicated in Table 4, it was surprisingly and unexpectedly discovered that the Peak 4/3 ratio for each of the samples (9)-(11) including HIDS were relatively higher than all of the samples (6)-(8) including IDS. This is particularly surprising as the chemical structures of IDS and HIDS are similar; and thus, the performance, efficacy, and/or results are expected to be relatively similar to one another. Without being bound by theory, it is believed that the additional hydroxyl group in the alpha position stabilizes the anionic carboxylate group via electronic induction, thereby reducing the alkalinity of the anion. The reduction in alkalinity yields a weaker interaction with the cationic aluminum salts. The results further indicate that HIDS exhibits relatively greater stability with respect to the aluminum clusters as compared to IDS.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A composition, comprising:
an antiperspirant active comprising aluminum;
water; and
a preservative system, wherein the preservative system consists essentially of $Na_4$-HIDS (tetrasodium 3-hydroxy-2,2'-iminodisuccinate); and
wherein the antiperspirant active comprises aluminum chlorohydrate (ACH), and
wherein the $Na_4$-HIDS is present in an amount of from 0.1 weight % to 0.2 weight % of the composition making the composition to exhibit an SEC chromatogram having the highest SEC 4/3 Peak Ratio among the SEC 4/3 Peak Ratios for the same compositions but having as the preservative system the $Na_4$-HIDS or $Na_4$-IDS (tetrasodium iminodisuccinate) in amounts of 0.1-0.25 weight % of the compositions.

2. The composition of claim 1, wherein the preservative system is free of ethylenediaminetetraacetic acid (EDTA) or salts thereof.

3. The composition of claim 1, wherein the preservative system consists of $Na_4$-HIDS present in an amount of 0.1 weight % of the composition.

4. The composition of claim 1, wherein the $Na_4$-HIDS is present in an amount of 0.1 weight % of the composition making the composition to exhibit an SEC chromatogram having the highest SEC Peak 4 area among the SEC Peak 4 areas for the same compositions but having as the preservative system the $Na_4$-HIDS in an amount of 0.1-0.8 weight % or $Na_4$-EDTA (tetrasodium EDTA) in an amount of 0.2 weight %, of the compositions.

5. The composition of claim 1, wherein the composition is an aqueous liquid in the form of a roll-on.

6. The composition of claim 1, further comprising a deodorant active.

7. The composition of claim 1, wherein the composition is an oil in water liquid roll-on.

8. The composition of claim 1, wherein the composition is a water in oil gel.

9. The composition of claim 1, wherein the composition is a water in oil cream.

10. The composition of claim 1, wherein the composition has a total solids content of about 25 weight % or less.

11. The composition of claim 1, wherein the water is present in an amount that is at least about 20 weight % by weight of the composition.

12. A method comprising, applying the composition of claim 1 to an axillary area of a person.

* * * * *